(12) United States Patent
Speeg et al.

(10) Patent No.: US 8,622,924 B2
(45) Date of Patent: Jan. 7, 2014

(54) NEEDLE TIP FOR BIOPSY DEVICE

(75) Inventors: Trevor W. V. Speeg, Williamsburg, OH (US); Peter Morgan, Great Shelford (GB); John A. Hibner, Mason, OH (US); Lee E. Reichel, Springboro, OH (US); William A. Garrison, Springdale, OH (US); Gavin M. Monson, Oxford, OH (US); Michael E. Johnson, West Chester, OH (US); Robert F. Weikel, Jr., Hamilton, OH (US); Michael R. Ludzack, Maineville, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 989 days.

(21) Appl. No.: 12/038,359

(22) Filed: Feb. 27, 2008

(65) Prior Publication Data

US 2009/0216152 A1 Aug. 27, 2009

(51) Int. Cl.
*A61B 10/00* (2006.01)

(52) U.S. Cl.
USPC .......................... 600/564; 600/566; 600/567

(58) Field of Classification Search
USPC ................................................. 600/562–568
See application file for complete search history.

(56) References Cited

U.S. PATENT DOCUMENTS

| | | | |
|---|---|---|---|
| 4,712,548 A * | 12/1987 | Enstrom | 606/181 |
| 5,477,862 A | 12/1995 | Haaga | |
| 5,526,822 A | 6/1996 | Burbank et al. | |
| 5,775,333 A | 7/1998 | Burbank et al. | |
| 5,928,164 A | 7/1999 | Burbank et al. | |
| 5,980,469 A | 11/1999 | Burbank et al. | |
| 6,086,544 A | 7/2000 | Hibner et al. | |
| 6,387,056 B1 * | 5/2002 | Kieturakis | 600/565 |
| 6,758,824 B1 | 7/2004 | Miller et al. | |
| 7,018,343 B2 | 3/2006 | Plishka | |
| 7,322,940 B2 | 1/2008 | Burbank et al. | |
| 7,438,692 B2 | 10/2008 | Tsonton et al. | |
| 7,569,053 B2 | 8/2009 | Eggers et al. | |
| 2003/0109801 A1 | 6/2003 | Rhad et al. | |

(Continued)

FOREIGN PATENT DOCUMENTS

EP 1 356 772 10/2003

OTHER PUBLICATIONS

European Search Report dated May 15, 2009 for Application. No. 09250531.
U.S. Appl. No. 11/942,764, filed Nov. 20, 2007, Hibner.

(Continued)

*Primary Examiner* — Brian Szmal
*Assistant Examiner* — H. Q. Nguyen
(74) *Attorney, Agent, or Firm* — Frost Brown Todd LLC

(57) ABSTRACT

A biopsy device includes a body portion, a tip, at least one blade, and a cutter. The cannula defines at least one lumen. The cannula has a transverse aperture configured to receive tissue. The tip is located at the distal end of the cannula, and may include at least two concave surfaces. The blade extends longitudinally from the tip. A second blade may also extend longitudinally from the tip. Blades may be axially staggered relative to the cannula. Blades may also have lengths that differ from one another. In addition, a blade may have a pointed distal end, or may have a curved distal edge. The configuration of the blade and tip may provide reduced force to penetrate tissue. The blade and tip may produce a cut length that is greater than or equal to the length of the outer perimeter of the cannula.

20 Claims, 13 Drawing Sheets

(56) References Cited

U.S. PATENT DOCUMENTS

| | | |
|---|---|---|
| 2003/0109803 A1 | 6/2003 | Huitema et al. |
| 2005/0059905 A1* | 3/2005 | Boock et al. .............. 600/567 |
| 2005/0159677 A1 | 7/2005 | Shabaz et al. |
| 2006/0144548 A1 | 7/2006 | Beckman et al. |
| 2007/0032740 A1 | 2/2007 | Quick et al. |
| 2007/0032742 A1 | 2/2007 | Monson et al. |
| 2007/0118048 A1 | 5/2007 | Stephens et al. |

OTHER PUBLICATIONS

U.S. Appl. No. 11/942,785, filed Nov. 27, 2007, Hibner.
U.S. Appl. No. 11/964,811, filed Dec. 27, 2007, Hibner.
U.S. Appl. No. 11/965,048, filed Dec. 27, 2007, Hibner.
U.S. Appl. No. 11/952,393, filed Dec. 7, 2007, Ritchie et al.
U.S. Appl. No. 11/952,405, filed Dec. 7, 2007, Hibner et al.
U.S. Appl. No. 12/117,933, filed May 9, 2008, Johnson.

* cited by examiner

NEEDLE TIP FOR BIOPSY DEVICE

BACKGROUND

Biopsy samples have been obtained in a variety of ways in various medical procedures using a variety of devices. Biopsy devices may be used under stereotactic guidance, ultrasound guidance, MRI guidance, or otherwise. Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Provisional Patent Application Ser. No. 60/869,736, entitled "Biopsy System," filed Dec. 13, 2006; U.S. Provisional Patent Application Ser. No. 60/874,792, entitled "Biopsy Sample Storage," filed Dec. 13, 2006; and U.S. Non-Provisional patent application Ser. No. 11/942,785, entitled "Revolving Tissue Sample Holder for Biopsy Device," filed Nov. 21, 2007. The disclosure of each of the above-cited U.S. patents, U.S. patent application Publications, U.S. Provisional Patent Applications, and U.S. Non-Provisional Patent Application is incorporated by reference herein.

In some settings, including some of those where a biopsy device tip needs to penetrate the tissue of a patient, some users of biopsy devices may prefer that the tip penetrate tissue with relatively little force. In other words, in some settings, a user may prefer a first biopsy device over a second biopsy device due to the first biopsy device requiring less force for its tip to penetrate tissue than the force required for the tip of the second biopsy device to penetrate tissue. This preference may be heightened when the tissue is relatively dense or under other circumstances.

Some biopsy devices may have a needle portion that has a generally circular cross-section, a generally ovular cross-section, a generally elliptical cross-section, a "figure eight" type of cross section, or some other cross-section. Such needle portions may have a predefined outer perimeter about a longitudinal axis. In some settings, the ratio of the length of an incision in tissue to the length of the perimeter or circumference of a biopsy device needle may be indicative of the magnitude of the force required to push the needle into dense tissue. For instance, in some settings, a relatively higher ratio of incision length to outer perimeter length may yield rises in tissue dilation hoop stresses that are more ideal (e.g., lower rates of rise) than rises in tissue dilation hoop stresses obtained using a relatively lower ratio of incision length to outer perimeter length (e.g., higher rates of rise).

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
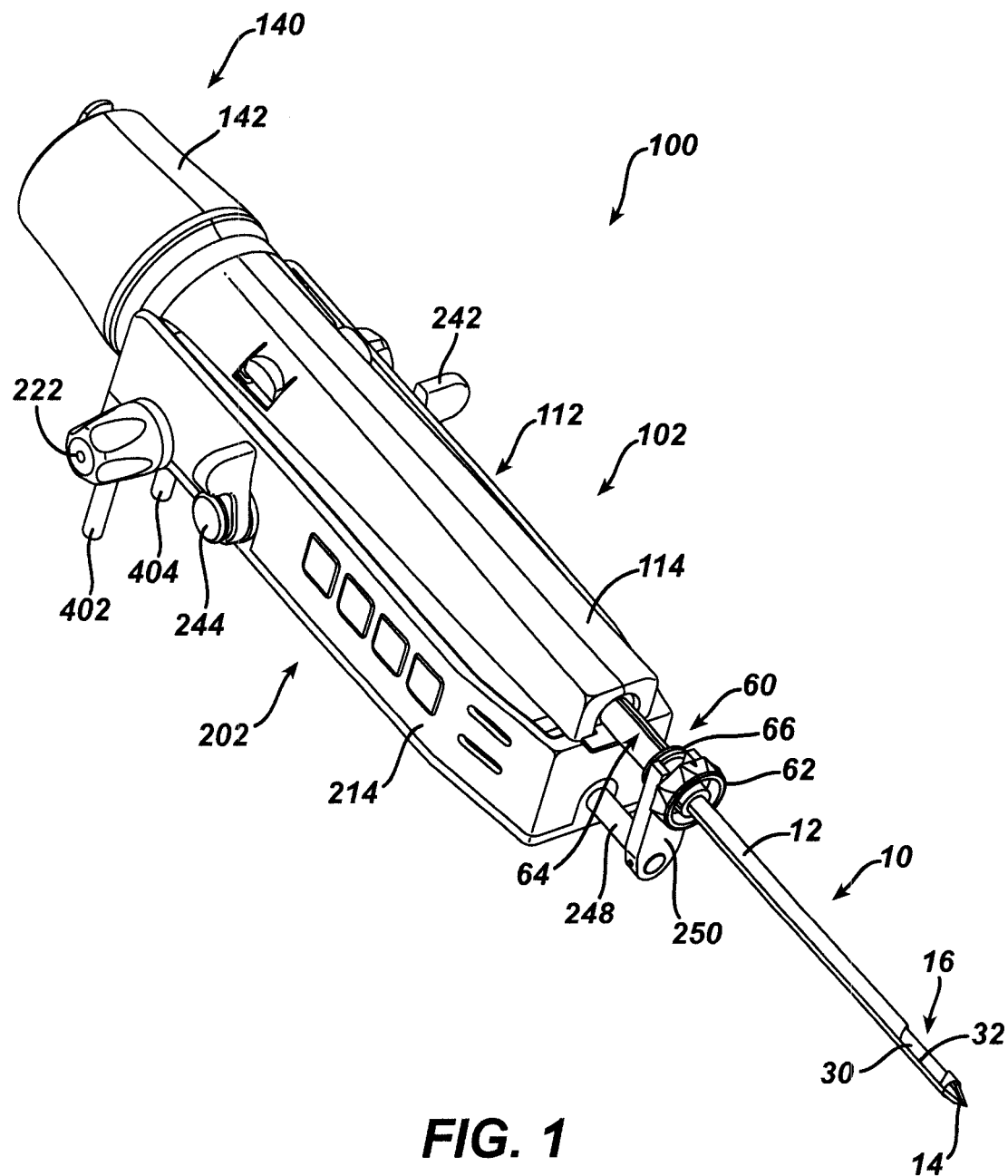
FIG. 1 depicts a perspective view of an exemplary assembled biopsy device, for use in a stereotactic setting.
Figure 2:
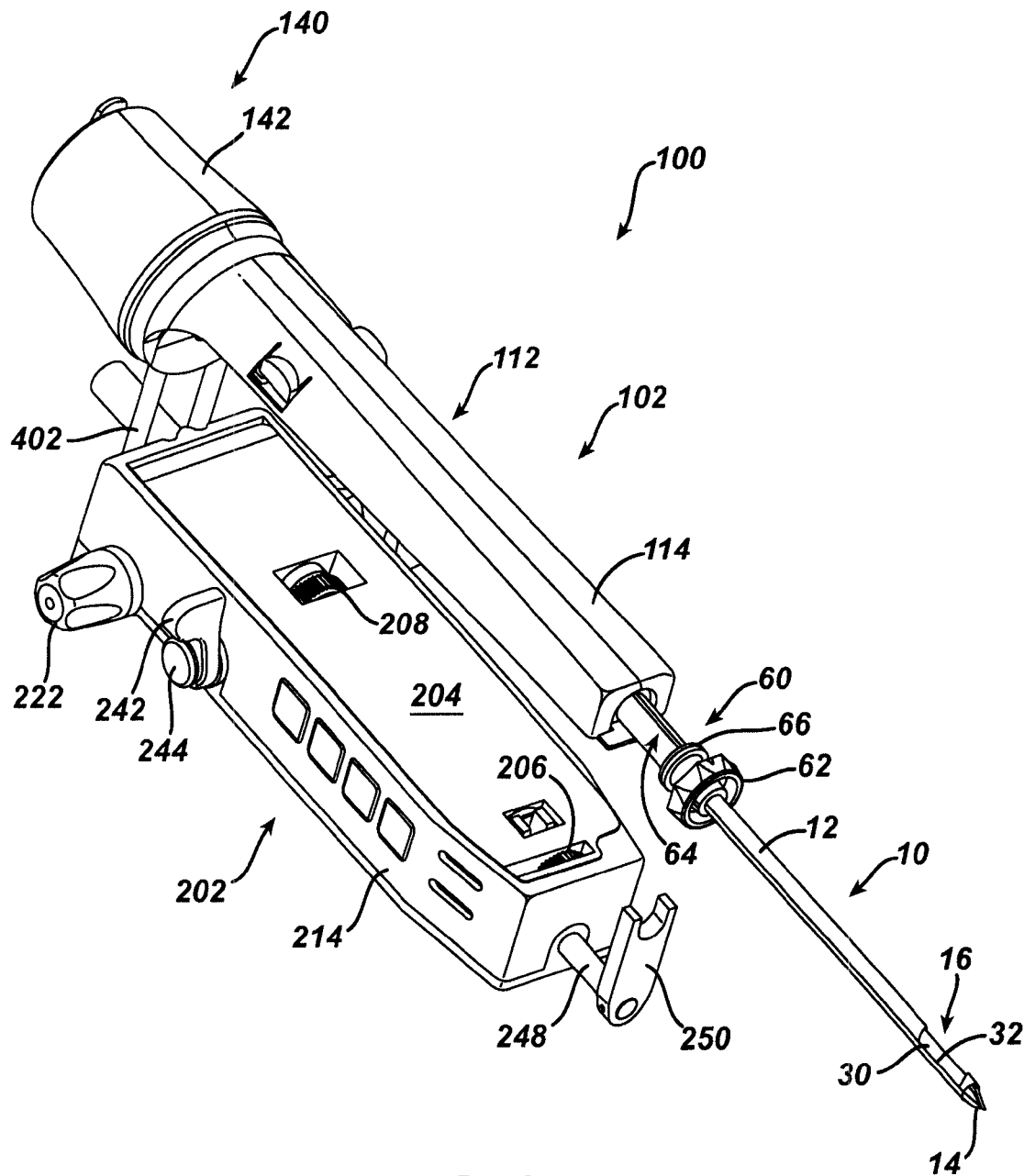
FIG. 2 depicts an exploded view of the biopsy device of FIG. 1, with the probe detached from the holster.
Figure 3:
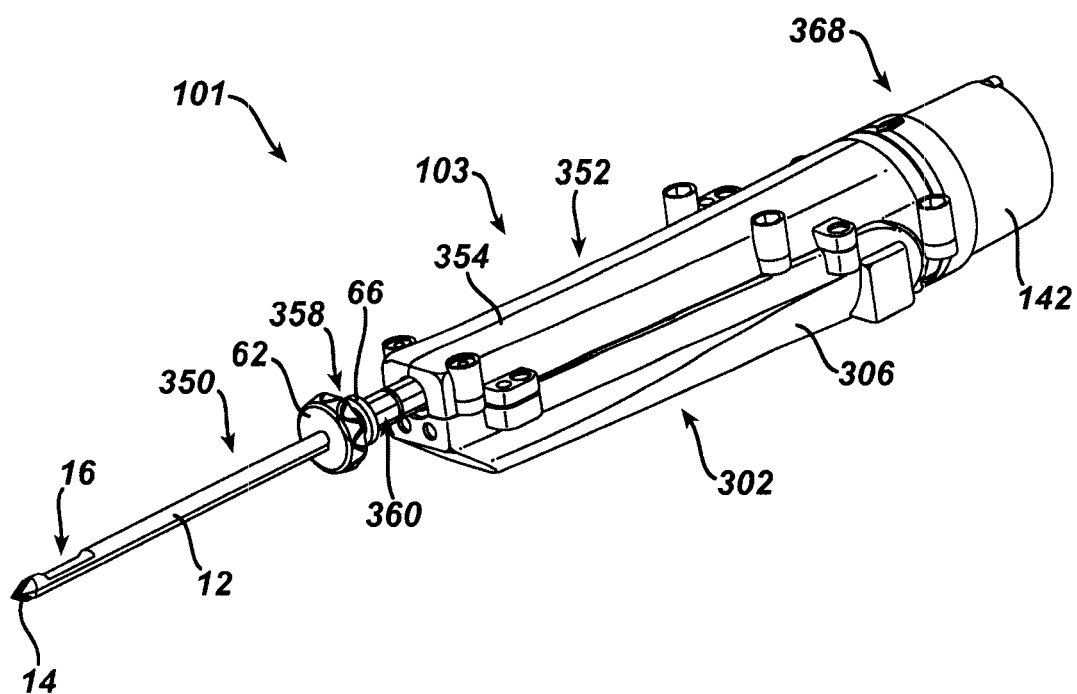
FIG. 3 depicts a perspective view of an exemplary assembled biopsy device, for use in an ultrasound setting.

As shown in FIGS. 1-2, an exemplary biopsy device (100) comprises a probe (102) and a holster (202). Similarly, as shown in FIGS. 2-3, another biopsy device (101) comprises a probe (103) and a holster (302). As will be described in greater detail below, each probe (102, 103) is separable from its corresponding holster (202, 302). By way of example only, probe (102, 103) may be provided as a disposable component, while holster (202, 302) may be provided as a reusable component. Use of the term "holster" herein should not be read as requiring any portion of probe (102, 103) to be inserted into any portion of holster (202, 302). Indeed, in some variations of biopsy devices (100, 101), probe (102, 103) may simply sit on holster (202, 302). In some other variations, a portion of holster (202, 302) may be inserted into probe (102, 103). Furthermore, in some biopsy devices (100, 101), probe (102, 103) and holster (202, 302) may be of unitary or integral construction, such that the two components cannot be separated or are not identifiable as different components. Still other suitable structural and functional relationships between probe (102, 103) and holster (202, 302) will be apparent to those of ordinary skill in the art in view of the teachings herein.

I. Exemplary Probe for Stereotactic Use

As shown in FIGS. 1-2, probe (102) comprises a needle portion (10) and a body portion (112). Body portion (112) comprises a cover member (114) and a base member (not shown). A tissue sample holder (140) is removably secured to base member (not shown), though tissue sample holder (140) may alternatively be secured to cover member (114) or some other component. A pair of tubes (402, 404) are coupled with probe (102) for communication of fluids (e.g., vacuum, saline, atmospheric air, pressurized air, etc.).

A. Exemplary Needle

In the present example, needle portion (10) comprises an outer cannula (12) having a tissue piercing tip (14) and a transverse tissue receiving aperture (16) located proximally from the tissue piercing tip (14). The interior of outer cannula (12) of the present example defines a cannula lumen (not shown) and a vacuum lumen (not shown), with a wall (not shown) separating the cannula lumen from the vacuum lumen. A plurality of external openings (22) are formed in outer cannula (12), and are in fluid communication with the vacuum lumen. Examples of openings that are similar to external openings (22) are disclosed in U.S. Pub. No. 2007/0032742, entitled "Biopsy Device with Vacuum Assisted Bleeding Control," published Feb. 8, 2007, the disclosure of which is incorporated by reference herein. Of course, as with other components described herein, external openings (22) are merely optional. The wall between the cannula lumen and the vacuum lumen also has a plurality of openings permitting fluid communication between the cannula lumen and the vacuum lumen in the present example, though such openings are also merely optional.

B. Exemplary Tissue Piercing Tips

Tissue piercing tip (14) is configured to penetrate tissue without requiring a high amount of force, and without requiring an opening to be preformed in the tissue prior to insertion of tip (14). Of course, in some versions of use, an incision or other opening may be formed in the tissue prior to insertion of tip (14). While a variety of merely exemplary tips (14) will be described in greater detail below, it should be understood that a variety of other tips (14) may be used. In some versions, a tip (14) may provide penetration in fibrous breast tissue with as little as approximately 20 newtons or approximately 4 pounds of force, if not less force, through and past a depth of at least 6 mm into the tissue. For instance, some versions of various tips (14) described herein may require less than approximately 20 newtons or less than approximately 4 pounds of force to penetrate through 10 mm, 20 mm, 30 mm, 40 mm, 50 mm, 60 mm, and/or greater depths of breast tissue. In other words, a tip (14) may penetrate through to any or all such depths without ever requiring an insertion force that exceeds approximately 20 newtons or approximately 4 pounds during such penetration. Some versions of various tips (14) described herein may even require less than approximately 15 newtons or less than approximately 3 pounds of force to penetrate through 10 mm, 20 mm, 30 mm, 40 mm, 50 mm, 60 mm, and/or greater depths of breast tissue. Alternatively, tips (14) may require any other suitable force to penetrate tissue to any desired depth.

In some versions, tip (14) comprises any one of the biopsy device needle tips disclosed in U.S. Provisional Application Ser. No. 60/917,375, filed May 11, 2007, entitled "Biopsy Device Needle Tip," the disclosure of which is incorporated by reference herein. Several other merely illustrative versions of tip (14) will be described in greater detail below, with reference to FIGS. 6-17, in which aperture (16) is not depicted as part of needle portion (10), though needle portions (10) including any of the tips shown and described herein may have an aperture (16).

Figure 6:
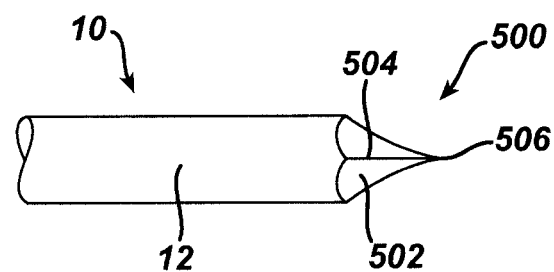
FIG. 6 depicts a plan view of an exemplary needle tip.
Figure 7:
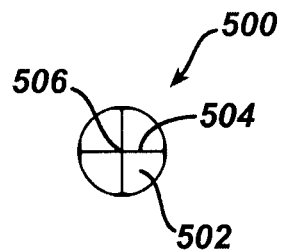
FIG. 7 depicts an end view of the needle tip of FIG. 6.
Figure 8:
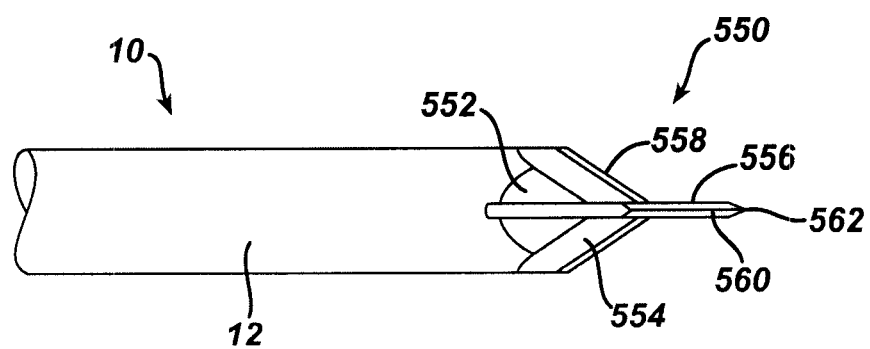
FIG. 8 depicts a plan view of another exemplary needle tip, at a first angular orientation.
Figure 9:
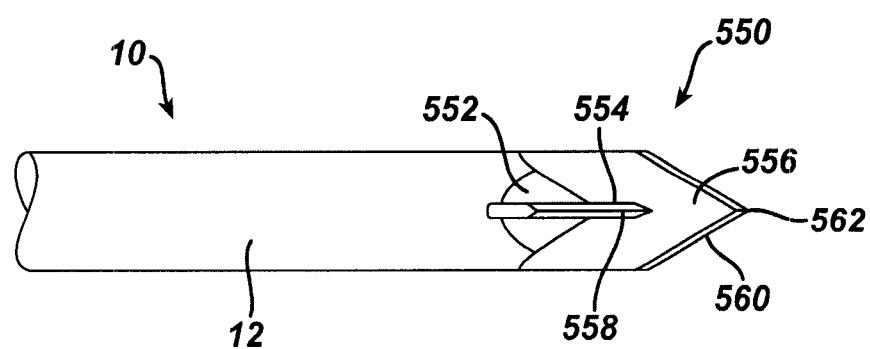
FIG. 9 depicts the needle tip of FIG. 8 at a second angular orientation, approximately 90 degrees from the first angular orientation.
Figure 10:
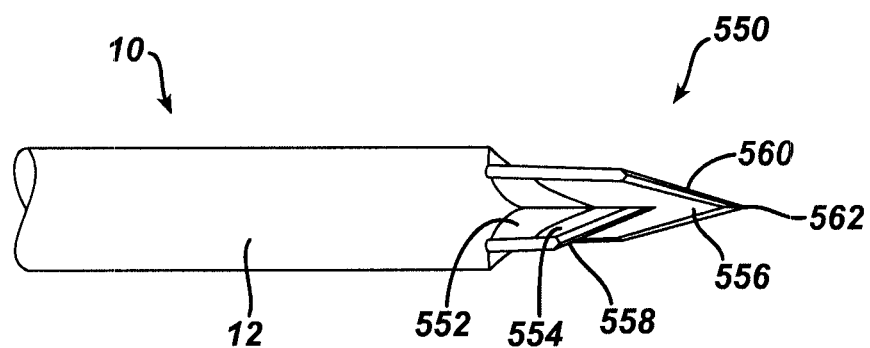
FIG. 10 depicts the needle tip of FIG. 8 at a third angular orientation, approximately between the first and second angular orientations.
Figure 11:
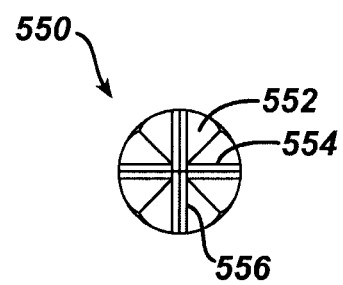
FIG. 11 depicts an end view of the needle tip of FIG. 8.

Another merely exemplary needle tip (500) that may be provided on a needle portion (10) is shown in FIGS. 6-7. As shown, needle tip (500) comprises four concave faces (502) that converge at a point (506). Concave faces (502) are "hollow ground" in this example, and may be formed using a bullet grinder or using any other device or technique. Alternatively, concave faces (502) may have a taper ground profile or any other suitable profile if a hollow ground profile is not desired.

In some versions, the tip (500) is integral and unitary with cannula (12), such that tip (500) is formed as an integral and unitary portion of cannula (12). In still other versions, the tip (500) and cannula (12) are formed separately then joined together. In such versions, the tip (500) may be ground and otherwise formed before the tip (500) is secured to cannula (12). Alternatively, the tip (500) may be ground after the tip (500) is secured to cannula (12).

Faces (502) are adjoined at shared edges (504). In the present example, each edge (504) has a length that is greater than or equal to the dimension of the outer perimeter or circumference of cannula (12). Edges (504) are angularly offset from one another by approximately 90 degrees in this example. However, in other variations, edges (504) may have any other suitable angular offset or offsets.

While needle tip (500) of this example comprises four faces (502), it will be appreciated that any other suitable number of faces may be used. For instance, the number of faces (502) may range from two to five, or fall within any other suitable range. Furthermore, while faces (502) in the present example all extend along the same axial length relative one another, it will be appreciated that faces (502) may extend along differing axial lengths. For instance, in a version with four faces (502), two opposing faces (502) may extend along a shorter axial length than the other two other opposing faces (502). Still other ways in which the axial length of faces (502) or other properties of faces (502) may be varied will be apparent to those of ordinary skill in the art in view of the teachings herein.

Another merely exemplary needle tip (550) that may be provided on a needle portion (10) is shown in FIGS. 8-11. As shown, needle tip (550) comprises four concave faces (552) and two blades (554, 556). Each blade (554, 556) has two sharpened edges (558, 560). Concave faces (552) may be formed and configured similar to faces (502) described above. Alternatively, faces (552) may have any other suitable configuration, including but not limited to substantially planar, convex, or any other configuration.

As shown, blade (554) is "shorter" than blade (556). In other words, edges (560) of blade (556) converge at a point (562) that is distal to edges (558) of blade (554). Blades (554, 556) are thus axially staggered along the longitudinal axis defined by needle portion (10). In other versions, however, blades (554, 556) are not axially staggered, and converge at a common distal-most point. It will also be appreciated that more than two blades (554, 556) may be used. To the extent that more than two blades (554, 556) are used, such blades may include two or more axially staggered blades and/or two or more blades that converge at a common distal-most point, including combinations of converging and axially staggered blades.

In addition, blades (554, 556) of the present example are positioned along angular mid-regions of faces (552), such that blades (554, 556) bisect each face (552). In other versions, blades (554, 556) extend along edges between faces (552). Other suitable relationships between blades (554, 556) and faces (552) will be apparent to those of ordinary skill in the art in view of the teachings herein. Blades (554, 556) of the present example are positioned such that edges (558, 560) are angularly spaced approximately 90 degrees from one another. However, in other variations, edges (558, 560) may have any other suitable angular offset or offsets.

In this example, each blade (554, 556) defines of angle of approximately 45 degrees. Of course, any other angle or angles may be used. In addition, tip (550) of the present example is configured such that cut length produced by tip (550) is greater than or equal to the perimeter length or circumference of cannula (12). It will be appreciated, however, that any other suitable dimensions or relationships between cannula (12) and tip (550) dimensions may be used.

In some versions, the blades (554, 556) are integral and unitary with needle tip (550), such that blades (554, 556) are formed as an integral and unitary portion of cannula (12). In still other versions, the blades (554, 556) and needle tip (550) are formed separately then joined together. For instance, the tip (550) may be ground and otherwise formed before the blades (554, 556) are secured tip (550). Similarly, blade (554) may be joined to tip (550) before blade (556) is joined to tip (550). Alternatively, blades (554, 556) may be joined together before being collectively joined to tip (550). Blades (554, 556) may be secured to tip (550) using interlocking features, welding, adhesives, or any other suitable structures or techniques. Slots (not shown) or other features may be provided in either or both of blades (554, 556) and/or tip (550) to accommodate their combination. Other ways in which tip (550) may be made will be apparent to those of ordinary skill in the art.

Figure 12:
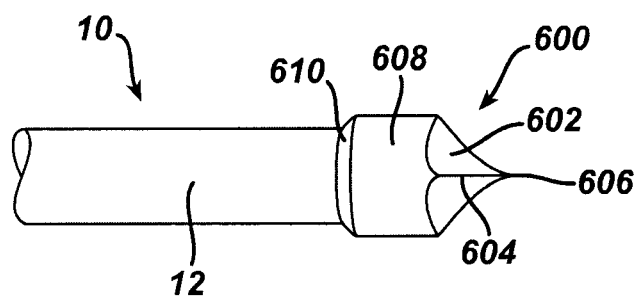
FIG. 12 depicts a plan view of another exemplary needle tip.
Figure 13:
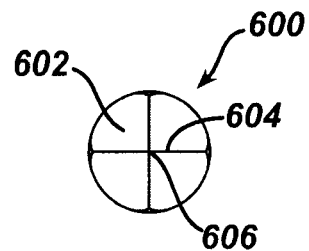
FIG. 13 depicts an end view of the needle tip of FIG. 12.

Another merely exemplary needle tip (600) that may be provided on a needle portion (10) is shown in FIGS. 12-13. As shown, needle tip (600) comprises four concave faces (602) that converge at a point (606). Like faces (502) described above, faces (602) may be "hollow ground," and may be formed using a bullet grinder or using any other device or technique. Alternatively, faces (602) may have a taper ground profile or any other suitable profile if a hollow ground profile is not desired.

Faces (602) are adjoined at shared edges (604). In the present example, each edge (604) has a length that is greater than or equal to the dimension of the outer perimeter or circumference of cannula (12). Edges (604) are angularly offset from one another by approximately 90 degrees in this example. However, in other variations, edges (604) may have any other suitable angular offset or offsets.

While needle tip (600) of this example comprises four faces (602), it will be appreciated that any other suitable number of faces may be used. For instance, the number of faces (602) may range from two to five, or fall within any other suitable range. Furthermore, while faces (602) in the present example all extend along the same axial length relative one another, it will be appreciated that faces (602) may extend along differing axial lengths. For instance, in a version with four faces (602), two opposing faces (602) may extend along a shorter axial length than the other two other opposing faces (602). Still other ways in which the axial length of faces (602) or other properties of faces (602) may be varied will be apparent to those of ordinary skill in the art in view of the teachings herein.

As is also shown in FIGS. 12-13, tip (600) is formed on a head (608), which has a greater diameter than that of cannula (12). The transition (610) from head (608) to cannula (12) is tapered in this example, though transition (610) may be generally curved or have any other suitable configuration. The larger diameter of head (608) in this example provides a cut length by tip (600) that is substantially larger than the perimeter or circumference of cannula (12), which may reduce the force required for the tip (600) and cannula (12) to penetrate tissue.

In some versions, the tip (600) is integral and unitary with cannula (12), such that tip (600) is formed as an integral and unitary portion of cannula (12). In still other versions, the tip (600) and cannula (12) are formed separately then joined together. In such versions, the tip (600) may be ground and otherwise formed before the tip (600) is secured to cannula (12). Alternatively, the tip (600) may be ground after the tip (600) is secured to cannula (12). Furthermore, head (608) may be removable from cannula (12), such that a variety of sizes of heads (608) and tips (600 may be secured to a cannula (12).

Figure 14:
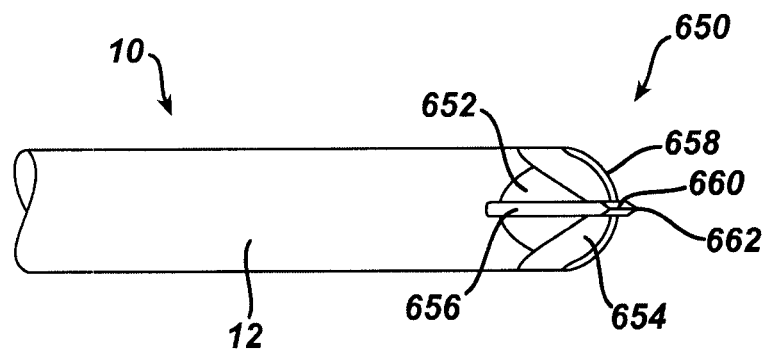
FIG. 14 depicts a plan view of another exemplary needle tip, at a first angular orientation.
Figure 15:
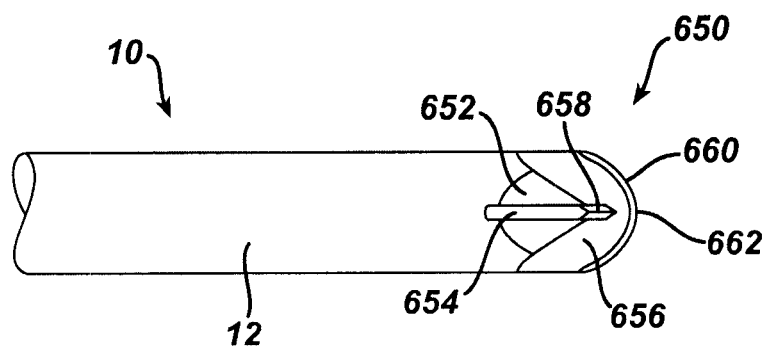
FIG. 15 depicts the needle tip of FIG. 14 at a second angular orientation, approximately 90 degrees from the first angular orientation.
Figure 16:
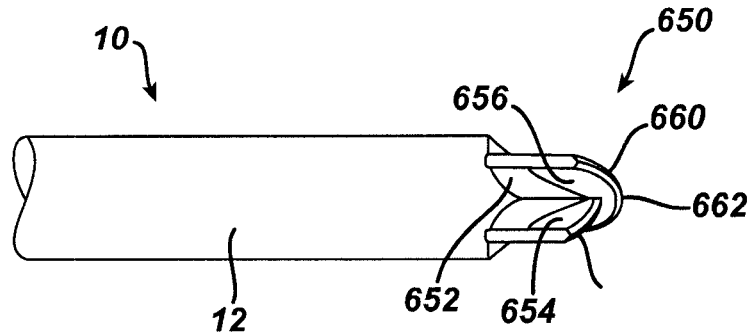
FIG. 16 depicts the needle tip of FIG. 14 at a third angular orientation, approximately between the first and second angular orientations.

Another merely exemplary needle tip (650) that may be provided on a needle portion (10) is shown in FIGS. 14-16. As shown, needle tip (650) comprises four concave faces (652) and two blades (654, 656). Each blade (654, 656) has two sharpened edges (658, 660). Concave faces (652) may be formed and configured similar to faces (502, 552, 602) described above. Alternatively, faces (652) may have any other suitable configuration, including but not limited to substantially planar, convex, or any other configuration.

As shown, blade (654) is "shorter" than blade (656). In other words, edge (660) of blade (656) reaches a distal-most a point (662) that is distal to the distal-most point (658) reached by blade (654). Blades (654, 656) are thus axially staggered along the longitudinal axis defined by cannula (12). In other versions, however, blades (654, 656) are not axially staggered, and reach a common distal-most point. It will also be appreciated that more than two blades (654, 656) may be used. To the extent that more than two blades (654, 656) are used, such blades may include two or more axially staggered blades and/or two or more blades that reach a common distal-most point, including combinations of converging and axially staggered blades.

In addition, blades (654, 656) of the present example are positioned along angular mid-regions of faces (652), such that blades (654, 656) bisect each face (652). In other versions, blades (654, 656) extend along edges between faces (652). Other suitable relationships between blades (654, 656) and faces (652) will be apparent to those of ordinary skill in the art in view of the teachings herein. Blades (654, 656) of the present example are positioned such that edges (658, 660) are angularly spaced approximately 90 degrees from one another. However, in other variations, edges (658, 660) may have any other suitable angular offset or offsets.

In this example, each blade (654, 656) may define of arc having any suitable radius of curvature. Having blades (654, 656) curved may reduce force spikes and allow for a relatively smoother insertion of needle portion (10) and tip (650), compared to some other needles and tips. In addition, tip (650) of the present example is configured such that cut length produced by tip (650) is greater than or equal to the perimeter or circumference of cannula (12). It will be appreciated, however, that any other suitable dimensions or relationships between cannula (12) and tip (650) dimensions may be used.

In some versions, the blades (654, 656) are integral and unitary with needle tip (650), such that blades (654, 656) are formed as an integral and unitary portion of cannula (12). In still other versions, the blades (654, 656) and needle tip (650) are formed separately then joined together. For instance, the tip (650) may be ground and otherwise formed before the blades (654, 656) are secured tip (650). Similarly, blade (654) may be joined to tip (650) before blade (656) is joined to tip (650). Alternatively, blades (654, 656) may be joined together before being collectively joined to tip (650). Blades (654, 656) may be secured to tip (650) using interlocking features, welding, adhesives, or any other suitable structures or techniques. Slots (not shown) or other features may be provided in either or both of blades (654, 656) and/or tip (650) to accommodate their combination. Other ways in which tip (650) may be made will be apparent to those of ordinary skill in the art.

Figure 17:
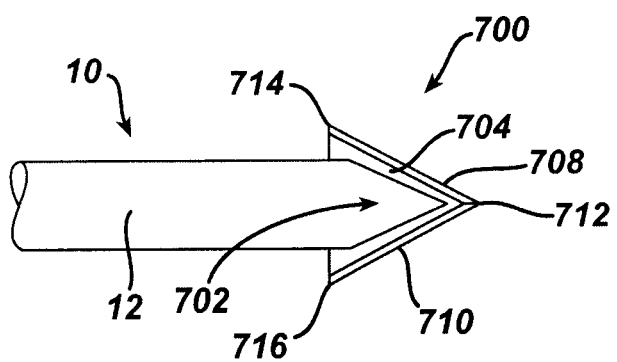
FIG. 17 depicts a plan view of another exemplary needle tip.
Figure 18:
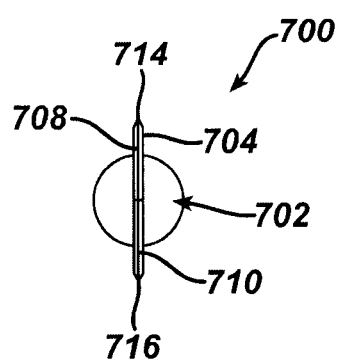
FIG. 18 depicts an end view of the needle tip of FIG. 17.

Another merely exemplary needle tip (700) that may be provided on a needle portion (10) is shown in FIGS. 17-18. As shown, needle tip (700) comprises a conical distal region (702) and a blade (704). In other versions, conical distal region (702) is instead a plurality of concave faces (e.g., similar to faces (502) described above), a plurality of planar faces, is convexly rounded, or has any other suitable configuration.

Blade (704) in this example has two sharpened edges (708, 710). Edges (708, 710) converge at a distal-most point (712); and each edge (708, 710) also terminates at a respective end point (714, 716). End points (714, 716) are separated by a distance that is greater than the diameter of cannula (12), giving tip (700) an arrowhead type of configuration. In some versions, end points (714, 716) are separated by a distance that is greater than or equal to the circumference or perimeter of cannula (12). The distance between end points (714, 716) may be regarded as defining a width of blade (704). Blade (704) may have a width that is small enough such that access to tumors is not impaired and such that the likelihood of a pneumo-thorax condition is not increased; yet large enough to reduce the force needed for needle portion (10) to penetrate tissue relative to a needle portion (10) that lacks a blade (704) having such a width. A blade (704) width may be selected based on a variety of considerations, including but not limited to tissue density. Blade (704) may also provide improved ultrasound visibility perpendicular to the largest dimension of blade (704).

In some versions, an additional blade (not shown) may be provided on tip (700). Such a blade may have a similar length and/or position along the longitudinal axis defined by needle portion (10) as blade (704). Alternatively, blade (704) and an additional blade may be longitudinally staggered along the axis defined by needle portion (10), similar to blades (554, 556) described above. Furthermore, an additional blade may be angularly separated relative to blade (704) by approximately 90 degrees. In still other variations, a plurality of blades are included with blade (704). In any of these versions, additional blades may have a width that is the same as or different from the width of blade (704). Similarly, an additional blade may have a width that is approximately equal to the diameter of cannula (12). Still other ways in which one or more additional blades may be incorporated into tip (700) will be apparent to those of ordinary skill in the art in view of the teachings herein.

In this example, blade (704) defines of angle of approximately 45 degrees. Of course, any other angle or angles may be used. In addition, tip (700) of the present example is configured such that cut length produced by tip (700) is greater than or equal to the perimeter or circumference of cannula (12). It will be appreciated, however, that any other suitable dimensions or relationships between cannula (12) and tip (700) dimensions may be used.

In some versions, blade (704) is integral and unitary with needle tip (700), such that blade (704) is formed as an integral and unitary portion of cannula (12). In still other versions, blade (704) and needle tip (700) are formed separately then joined together. Blade (704) may be secured to tip (700) using interlocking features, welding, adhesives, or any other suitable structures or techniques. Slots (not shown) or other features may be provided in blade (704) and/or tip (700) to accommodate their combination. Furthermore, tip (700) may be integrally and unitarily formed with cannula (12); or may be formed separately from cannula (12) then secured to the distal end of cannula (12). Other ways in which tip (700) may be made will be apparent to those of ordinary skill in the art.

Other suitable configurations for a tissue piercing tip (14) or other components of needle portion (10) will be apparent to those of ordinary skill in the art in view of the teachings herein.

C. Exemplary Cannula Modifications

In addition to or in lieu of providing any of the various versions of tip (14) described herein, cannula (12) may be subject to various modifications. Such modifications may reduce the force that is required for needle portion (10) to penetrate into tissue. One such modification may include applying a carbon or hydrophilic coating to the outer surface of cannula (12) and/or tip (14). Alternatively, any other coating or treatment may be applied to cannula (12) and/or tip (14). Several additional modifications will be described in greater detail below, while others will be apparent to those of ordinary skill in the art in view of the teachings herein.

Figure 19:
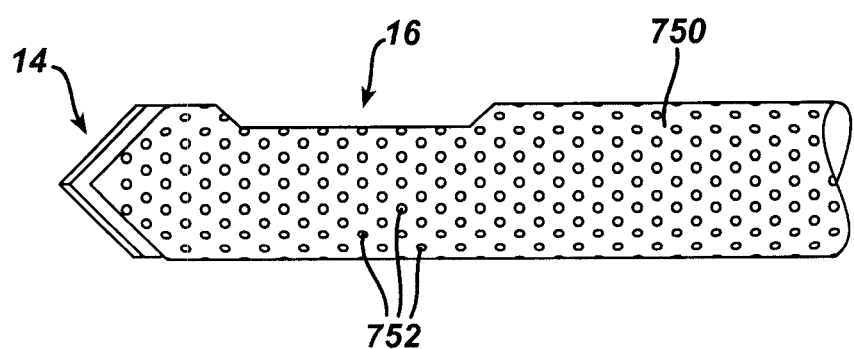
FIG. 19 depicts a plan view of an exemplary modified cannula.

One merely illustrative modified cannula (750) is shown in FIG. 19. In this example, cannula (750) is subject to shot peening, which results in a plurality of dimples (752) being formed in cannula (12). It will be appreciated that, in some contexts, a cannula (12) that has a smooth electropolished outside surface may exhibit some degree of adherence to tissue as it penetrates the tissue. Such adherence may result in a relatively increased force that is required for a needle portion (10) that has such a cannula (12) to penetrate the tissue. By contrast, dimples (752) may reduce such a drag effect (e.g., by reducing the contact surface), such that modified cannula (750) requires relatively less force for needle portion (10) to penetrate tissue. Dimples (752) may be provided along any suitable length of cannula (750).

Shot peening of cannula (750) may be accomplished using a variety of media or techniques. By way of example only, the outer surface of cannula (750) may be shot peened with small spherical media (e.g., beads, etc.), such as sand, metal, glass, or any other suitable material, including combinations of material. Alternatively, dimples (752) may be produced using any other suitable process. Furthermore, cannula (750) may be roughened without necessarily resulting in dimples. Other ways in which a cannula (750) may be treated will be apparent to those of ordinary skill in the art in view of the teachings herein.

Figure 20:
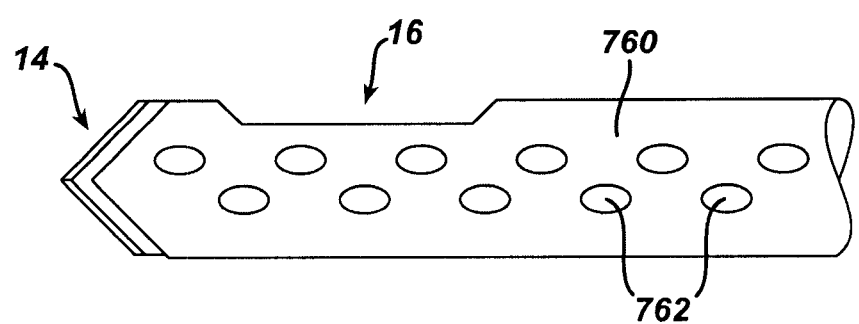
FIG. 20 depicts a plan view of another exemplary modified cannula.

Another merely illustrative modified cannula (760) is shown in FIG. 20. In this example, cannula (760) has a plurality of scallops (762) formed therein. Scallops (762) may be formed using a variety of processes, including but not limited to cutting or grinding. Similar to dimples (752), scallops (762) may reduce the force that is required for a needle portion (10) having such a cannula (760) to penetrate tissue (e.g., by reducing the contact surface). Scallops (762) may be provided along any suitable length of cannula (760), and may have any suitable spacing and configuration.

Figure 21:
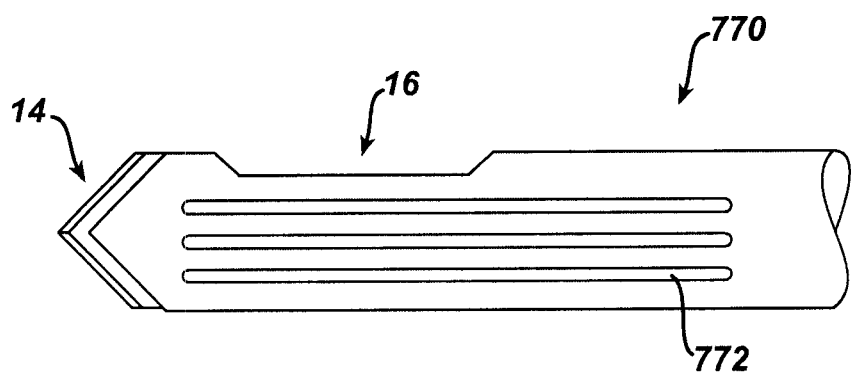
FIG. 21 depicts a plan view of another exemplary modified cannula.

Yet another merely illustrative modified cannula (770) is shown in FIG. 21. In this example, cannula (770) has a plurality of longitudinal grooves (772) formed therein. Grooves (772) may be formed using a variety of processes, including but not limited to cutting or grinding. Similar to dimples (752) and scallops (762), grooves (772) may reduce the force that is required for a needle portion (10) having such a cannula (770) to penetrate tissue (e.g., by reducing the contact surface). Grooves (772) may extend along any suitable length of cannula (770), and may have any suitable spacing and configuration. Grooves (772) may also be formed in any suitable orientation(s) (e.g., orientations other than longitudinal).

D. Exemplary Cutter

A hollow cutter (not shown) is disposed within the cannula lumen of cannula (20). The interior of the cutter defines a cutter lumen, such that fluid and tissue may be communicated through the cutter via the cutter lumen. The cutter is configured to rotate within the cannula lumen and translate axially within the cannula lumen. Suitable mechanisms that may be provided for causing the cutter to rotate and translate are disclosed in U.S. Non-Provisional patent application Ser. No. 11/942,764, filed Nov. 20, 2007, and entitled "Vacuum Timing Algorithm for Biopsy Device," the disclosure of which is incorporated by reference herein; while other suitable mechanisms will be apparent to those of ordinary skill in the art in view of the teachings herein. The cutter may be configured to sever a biopsy sample from tissue protruding through transverse aperture (16) of outer cannula (12). The cutter is further configured to permit severed tissue samples to be communicated proximally through the cutter lumen. Merely illustrative examples of such severing and proximal communication are described in U.S. Pat. No. 5,526,822, the disclosure of which is incorporated by reference herein, though any other suitable structures or techniques may be used for severing and/or communicating tissue samples within a biopsy system (2).

In addition, suitable components of, structures for, relationships between, and configurations for cannula (20) and a cutter are disclosed in U.S. Non-Provisional patent application Ser. No. 11/942,764, filed Nov. 20, 2007, and entitled "Vacuum Timing Algorithm for Biopsy Device," the disclosure of which is incorporated by reference herein. Of course, any other suitable components, structures, or configurations may be used.

E. Exemplary Needle Hub

As shown in FIGS. 1-2, a needle hub (60) is secured to outer cannula (12), and comprises a thumbwheel (62) and a sleeve portion (64) extending proximally from thumbwheel (62). Needle hub (60) of the present example is overmolded about a proximal portion of outer cannula (12), though needle hub (60) may be formed and/or secured relative to outer cannula (12) using any other suitable techniques (e.g., set screws, adhesives, etc.). Furthermore, while needle hub (60) of the present example is formed of a plastic material, any other suitable material or combination of materials may be used.

Needle hub (60) may include an interior portion that is in fluid communication with the vacuum lumen of outer cannula (12). Needle hub (60) may further be in fluid communication with a manifold (not shown) that is in further communication with either or both of tubes (402, 404). Suitable ways in which needle hub (60) may be in fluid communication with a lumen in outer cannula (12) are disclosed in U.S. Non-Provisional patent application Ser. No. 11/942,764, filed Nov. 20, 2007, and entitled "Vacuum Timing Algorithm for Biopsy Device," the disclosure of which is incorporated by reference herein. Of course, any other suitable components, structures, or configurations may be used.

Thumbwheel (62) is operable to rotate outer cannula (12) about its longitudinal axis, relative to cover member (114) and base member (116). For instance, thumbwheel (62) may be used to orient aperture (16) to a number of desired orientations about the longitudinal axis defined by outer cannula (12). Such multiple orientations may be desirable, by way of example only, to obtain a plurality of tissue samples from a biopsy site, without requiring the needle portion (10) to be removed from the patient during the acquisition of such a plurality of tissue samples. An illustrative example of such rotation and acquisition of multiple tissue samples is disclosed in U.S. Pat. No. 5,526,822, the disclosure of which is incorporated by reference herein. Other ways in which multiple tissue samples may be obtained at various locations will be apparent to those of ordinary skill in the art in view of the teachings herein. For instance, rotation of outer cannula (12) may be motorized or automated. As another non-exhaustive example, an entire biopsy device (100) may be rotated during acquisition of tissue samples, without necessarily removing biopsy device (100) from the patient during such rotation and tissue sample acquisition, to obtain tissue samples from various orientations about the longitudinal axis defined by outer cannula (12).

F. Exemplary Tissue Sample Holder

In the present example, a tissue sample holder (140) is provided at the end of body portion (112) of probe (102). Tissue sample holder (140) comprises a cup (142), a rotatable manifold (not shown), and a plurality of removable sample trays (not shown) with a plurality of tissue sample chambers (not shown). Each tissue sample chamber is configured to separately hold a tissue sample communicated proximally through the cutter lumen, such that tissue sample holder (140) may separately hold a plurality of tissue samples. In particular, the manifold is configured to rotate to selectively index a tissue sample chamber relative to the cutter lumen. Manifold is further configured to communicate a vacuum from tube (404) to the cutter lumen, regardless of which tissue sample chamber is indexed relative to the cutter lumen. Suitable components and structures for and methods of operating a tissue sample holder (140) are disclosed in U.S. Non-Provisional patent application Ser. No. 11/942,764, filed Nov. 20, 2007, and entitled "Vacuum Timing Algorithm for Biopsy Device," the disclosure of which is incorporated by reference herein. Of course, any other suitable components, structures, or configurations may be used.

II. Exemplary Holster for Stereotactic Use

As shown in FIGS. 1-2, a holster (202) comprises a top cover (204), through which a portion of each of gears (206, 208) is exposed, and side panels (214). Holster (202) of this example further comprises a needle rotation mechanism (not shown), a needle firing mechanism (240), a cutter drive mechanism (not shown), and a tissue holder rotation mechanism (not shown). The cutter drive mechanism is operable to cause the cutter to rotate and translate; while the tissue holder rotation mechanism is operable to cause at least a portion of the tissue sample holder (140) to rotate. Suitable components and structures that may be used to provide a cutter drive mechanism and a tissue holder rotation mechanism are disclosed in U.S. Non-Provisional patent application Ser. No. 11/942,764, filed Nov. 20, 2007, and entitled "Vacuum Timing Algorithm for Biopsy Device," the disclosure of which is incorporated by reference herein. Of course, any other suitable components, structures, or configurations may be used.

Alternatively, either or both of a cutter drive mechanism or a tissue holder rotation mechanism may simply be omitted altogether.

As noted above, holster (202) of the present example is configured to be coupled with a biopsy probe (102), such as biopsy probe (102) described above, to provide a biopsy device (100). In addition, holster (202) is configured to be mounted to a table, fixture, or other device, such as for use in a stereotactic or X-ray setting. However, it will be appreciated in view of the disclosure herein that holster (202) may be used in a variety of other settings and combinations.

A. Exemplary Needle Rotation Mechanism

In the present example, the needle rotation mechanism comprises a pair of knobs (222). Rotation of one or both of knobs (222) will result in rotation of gear (206). Furthermore, when biopsy probe (102) is coupled with holster (202), gear (206) will mesh with a gear (not shown) of probe (102). Thus, when biopsy probe (102) is coupled with holster (202), rotation of one or both of knobs (222) will cause needle portion (10) of biopsy probe (102) to rotate. Suitable structures and components that may form a needle rotation mechanism are disclosed in U.S. Non-Provisional patent application Ser. No. 11/942,764, filed Nov. 20, 2007, and entitled "Vacuum Timing Algorithm for Biopsy Device," the disclosure of which is incorporated by reference herein. Of course, any other suitable components, structures, or configurations may be used. By way of example only, a motor (not shown) may be used to effect rotation of needle portion (10). In other versions, a needle rotation mechanism may simply be omitted altogether.

B. Exemplary Needle Firing Mechanism

As shown in FIG. 16, needle firing mechanism (240) of the present example comprises a pair of triggers (242), buttons (244), a firing rod (248), and a fork (250). Fork (250) is configured to engage sleeve portion (64) of needle hub (60) when biopsy probe (102) is coupled with holster (202). For instance, fork (250) may engage sleeve portion (64) between thumbwheel (62) and an annular projection (66). In the present example, engagement between fork (250) and sleeve portion (64) is such that sleeve portion (64) (and therefore, needle portion (10)) will translate longitudinally with fork (250). Fork (250) is coupled with a firing rod (248), such that fork (250) will translate longitudinally with firing rod (248).

Figure 22:
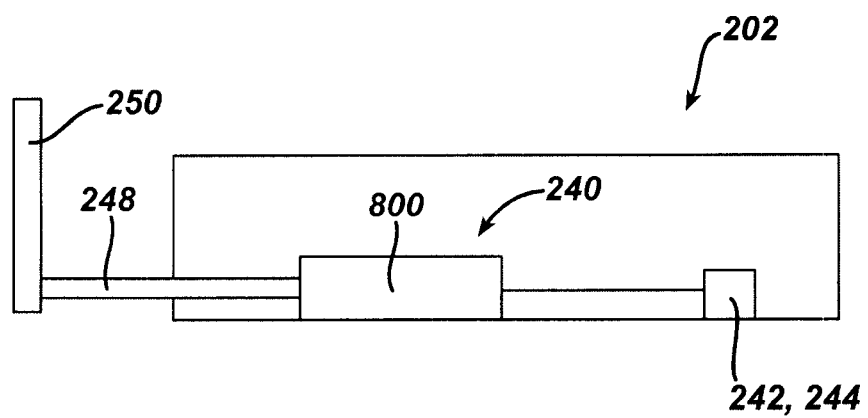
FIG. 22 depicts a schematic cross-sectional view of the holster of FIG. 1 with an exemplary needle firing mechanism.

As shown in FIG. 22, needle firing mechanism (240) of the present example further comprises a linear motor (800), which is communicatively coupled with firing rod (248). In some versions, firing rod (248) extends directly from linear motor (800). In other versions, one or more components (not shown) are provided between linear motor (800) and firing rod (248). For instance, a variety of gears, transmission components, etc. may be provided between linear motor (800) and firing rod (248). Suitable structures, components and configurations for providing communication from linear motor (800) to firing rod (248) will be apparent to those of ordinary skill in the art in view of the teachings herein.

In some versions, linear motor (800) comprises a brushless DC linear motor. Alternatively, any other suitable type of electric linear motor may be used. In other versions, linear motor (800) comprises a pneumatic motor. For instance, such a pneumatic motor may or may not include a pneumatic cylinder, a piston, and/or a variety of other components. Of course, any other type of linear motor may be used—electric, pneumatic, or otherwise.

It will be appreciated by those of ordinary skill in the art in view of the teachings herein that linear motor (800) may be selectively controlled with respect to a variety of parameters. For instance, a user may control the depth, acceleration, force, and/or velocity with which linear motor (800) actuates to fire needle portion (10) into tissue. In other words, a controller (not shown) may be used to control the velocity profile, position profile, and stopping point of linear motor (800), among other parameters associated with operation of linear motor (800). Particularly where a linear motor (800) of relatively high peak force is provided, a large envelope of velocity and position profiles may be available.

In some versions, a user may select a longitudinal position to which needle firing mechanism (240) should fire tip (14) or aperture (16) of needle portion (10). With such a longitudinal position being set before firing of needle portion (10), linear motor (800) may be activated to fire needle portion (10) accordingly, stopping needle portion (10) at the preselected position or distance. Needle portion (10) may be noiselessly brought to a stop through electromagnetic action, rather than by a mechanical stop. Alternatively, mechanical assistance may be provided for bringing needle portion (10) to a stop (e.g., a brake mechanism, etc.). Excess kinetic energy of needle portion (10) may silently be converted into heat. Preprogrammed velocity and position profiles may be maintained independently of the tissue or tumor characteristics. In other words, in some versions, acceleration of needle portion (10) may be controlled such that it does not exceed a rate that is greater than required to follow the desired position and velocity profiles.

Furthermore, with linear motor (800) being used to fire needle portion (10) into tissue, needle firing mechanism (240) may lack a spring or other resilient member for firing needle portion (10) into tissue. The absence of a spring or other resilient member may provide relatively quiet operation of needle firing mechanism (240), which may make a biopsy sample acquisition sequence less alarming to a patient in some settings. Alternatively, linear motor (800) may be assisted by a spring or other resilient member, with respect to either or both of distal or proximal translation of firing rod (248).

When a user is ready to fire needle portion (10), the user may push and hold one or both of triggers (242) forward, and may push one or both buttons (244) in while one or both of triggers (242) are held forward. Such actuation of trigger(s) (242) and button(s) (244) may cause firing of needle portion (10). In particular, Such actuation of trigger(s) (242) and button(s) (244) may activate motor (800) to translate firing rod (248) distally, which may effect firing of needle portion (10) distally into tissue. Such distal motion of needle portion (10) may be relatively sudden, and may be performed with a force sufficient to penetrate tissue with tip (14) of needle portion (10).

In other variations, a linear motor (800) is used to fire an entire holster (202). In still other variations, needle firing mechanism (240) lacks a linear motor (800) altogether. For instance, needle firing mechanism (240) may comprise one of the needle firing mechanisms disclosed in U.S. Pub. No. 2007/0032742, entitled "Biopsy Device with Vacuum Assisted Bleeding Control," published Feb. 8, 2007, the disclosure of which is incorporated by reference herein. Still other suitable components and configurations for a needle firing mechanism (240) will be apparent to those of ordinary skill in the art in view of the teachings herein, to the extent that a needle firing mechanism (240) is used at all.

III. Exemplary Probe for Ultrasound Use

Figure 4:
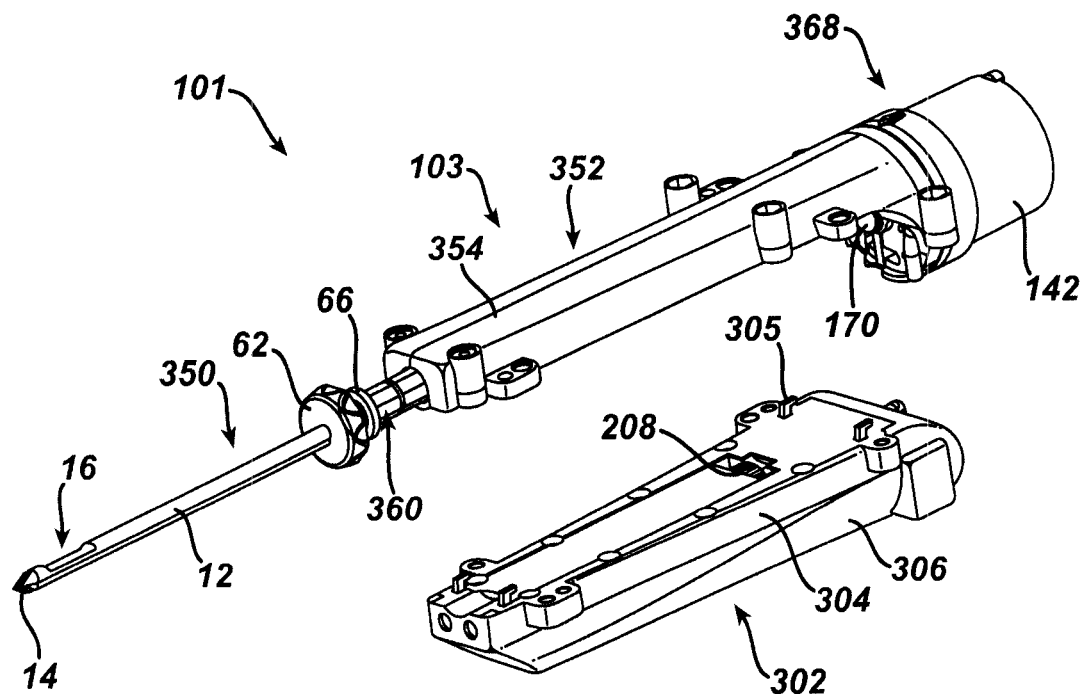
FIG. 4 depicts an exploded view of the biopsy device of FIG. 3, with the probe detached from the holster.
Figure 5:
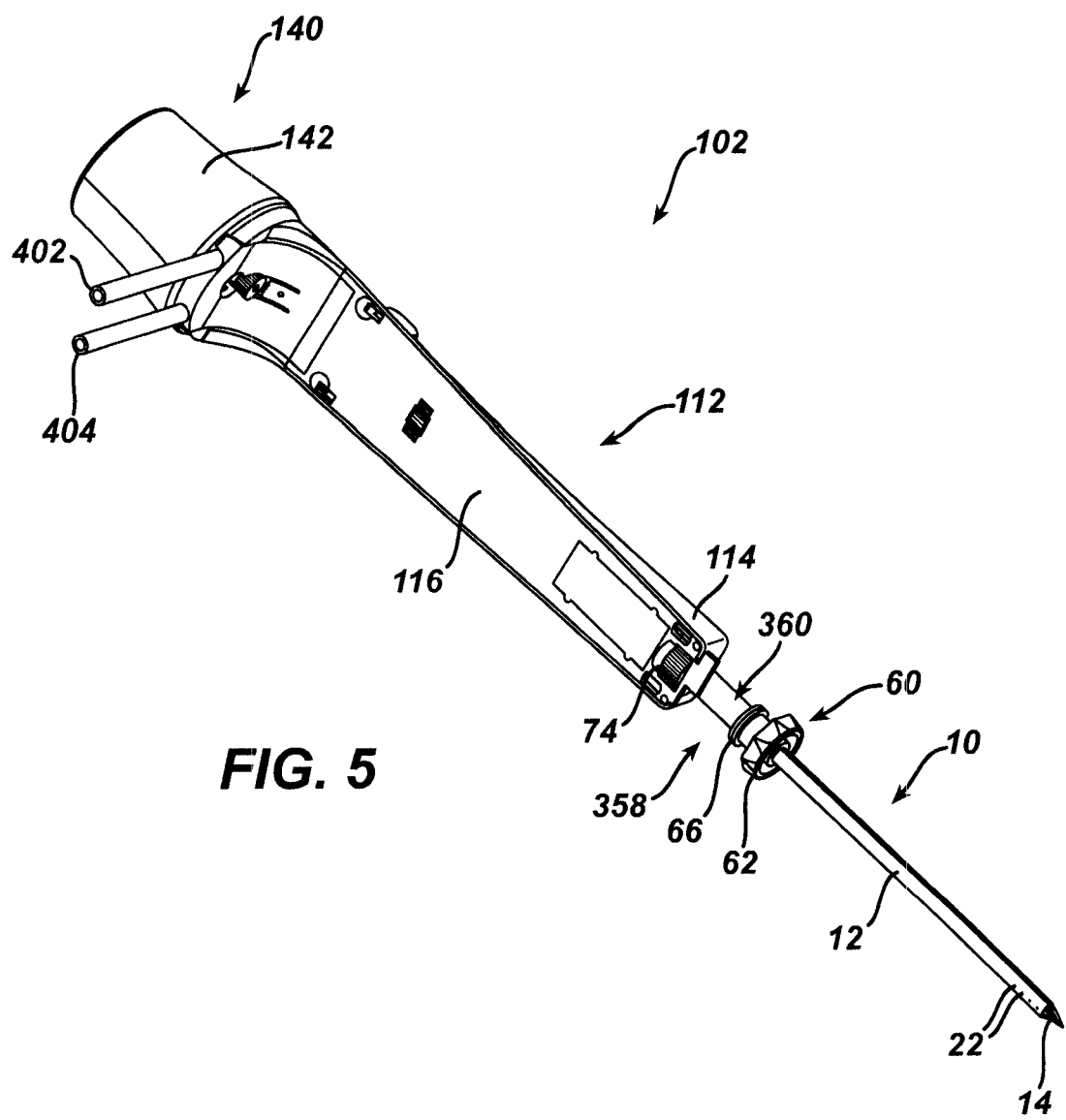
FIG. 5 depicts a bottom perspective view of the probe portion of FIG. 5.

As shown in FIGS. 3-5, an alternative biopsy probe (103) comprises a needle portion (350) and a body portion (352). Body portion (352) comprises a cover member (354) and a base member (356). A tissue sample holder (368) is removably secured to base member (356), though tissue sample holder (368) may alternatively be secured to cover member (354) or some other component. A pair of tubes (402, 404) are coupled with probe (103). As will also be described in greater detail below, and as noted above, biopsy probe (103) is configured to be coupled with a holster (302) to provide a biopsy device (101).

A. Exemplary Needle

In the present example, needle portion (350) comprises an outer cannula (12) having a tissue piercing tip (14) and a transverse tissue receiving aperture (16) located proximally from the tissue piercing tip (14). In this example, these components are essentially the same as the components bearing the same names and item numbers described above, so they will not be described in greater detail here. In other words, the features, properties, and components of outer cannula (12), tip (14), and aperture (16) as described above (including cannula lumen (20), vacuum lumen (40), wall (30), transverse openings (32), etc.) may be the same for needle portion (350) as they were described above with respect to needle portion (10). Of course, they may alternatively be varied in any suitable way, as desired.

B. Exemplary Tissue Piercing Tips

In some instances, those of ordinary skill in the art may find some of the various needle tips (14) that are disclosed herein as being particularly useful in probe (103). For instance, probe (103) may include any of the various tips described herein, such as those described with reference to FIGS. 6-18. Similarly, cannula (12) of probe (103) may be subject to any of the treatments or modifications described herein, such as those described with reference to FIGS. 19-21. As noted previously, such variations, treatments, and modifications of tip (14) and cannula (12) may facilitate penetration of needle portion (350) into tissue, such as by reducing the force that is required to penetrate tissue when compared to other tips (14) and cannulas (12). Such reduced force to penetrate may be particularly useful in the context of probe in the present example (103), as probe (103) is manipulated by a single hand of a user in some illustrative uses. In other words, biopsy device (101) may be grasped by a single hand of a user, and the user may insert needle portion (350) into tissue by using the single hand grasping biopsy device (101). Alternatively, biopsy device (101) may be used in a variety of other ways.

C. Exemplary Cutter

A hollow cutter in probe (103) may have the same relationship with needle portion (350) as the relationship described above between the cutter and needle portion (10); as well as all the same features, properties, and components as the cutter described above in the context of probe (102). Such aspects of the cutter will therefore not be repeated here. Alternatively, a cutter used with either probe (102, 103) may have any other features, properties, components, or relationships with needle portion (10) as desired.

D. Exemplary Needle Hub

As shown in FIGS. 3-5, a needle hub (358) is secured to outer cannula (12) of probe (103), and comprises a thumbwheel (62) and a sleeve portion (360) extending proximally from thumbwheel (62). Needle hub (358) of the present example is overmolded about a proximal portion of outer cannula (12), though needle hub (358) may be formed and/or secured relative to outer cannula (12) using any other suitable techniques (e.g., set screws, etc.). Furthermore, while needle hub (358) of the present example is formed of a plastic material, any other suitable material or combination of materials may be used.

Needle hub (358) may include an interior portion that is in fluid communication with the vacuum lumen of outer cannula (12). Needle hub (358) may further be in fluid communication with a manifold (not shown) that is in further communication with either or both of tubes (402, 404). Suitable ways in which needle hub (358) may be in fluid communication with a lumen in outer cannula (12) are disclosed in U.S. Non-Provisional patent application Ser. No. 11/942,764, filed Nov. 20, 2007, and entitled "Vacuum Timing Algorithm for Biopsy Device," the disclosure of which is incorporated by reference herein. Of course, any other suitable components, structures, or configurations may be used.

Thumbwheel (62) of sleeve portion (360) is essentially the same as, and may be operated in a manner similar to, thumbwheel (62) of sleeve portion (64) of probe (102) described above. Thumbwheel (62) will therefore not be discussed in any greater detail here. Of course, thumbwheel (62) may alternatively be varied in any suitable way, as desired, if not omitted altogether, in the case of either probe (102, 103).

E. Exemplary Tissue Sample Holder

In addition, a tissue sample holder (368) of probe (103) may be the same as or similar to tissue sample holder (140) described above. Alternatively, tissue sample holder (368) may include any tissue sample holder described in U.S. Non-Provisional patent application Ser. No. 11/942,764, filed Nov. 20, 2007, and entitled "Vacuum Timing Algorithm for Biopsy Device," the disclosure of which is incorporated by reference herein. Of course, any other suitable components, structures, or configurations may be used for tissue sample holder (368), to the extent that any tissue sample holder is used at all.

IV. Exemplary Holster for Ultrasound Use

As shown in FIGS. 3-4, an alternative holster (302) comprises a top housing member (304), through which a portion of each of gears (206, 208) is exposed, and a bottom housing member (306). A plurality of hook members (305) extend from top housing member (304) for selectively securing probe (103) to holster (302), though other structures or techniques may be used. Holster (302) of this example further comprises a cutter drive mechanism (not shown) and a tissue holder rotation mechanism (not shown). Suitable components and structures that may be used to provide a cutter drive mechanism and a tissue holder rotation mechanism are disclosed in U.S. Non-Provisional patent application Ser. No. 11/942,764, filed Nov. 20, 2007, and entitled "Vacuum Timing Algorithm for Biopsy Device," the disclosure of which is incorporated by reference herein. Of course, any other suitable components, structures, or configurations may be used. Alternatively, either or both of a cutter drive mechanism or a tissue holder rotation mechanism may simply be omitted altogether.

Holster (302) may include a user interface that permits a user to enter commands to operate at least a portion of biopsy device (101). Suitable user interfaces that may be so incorporated into holster (302) are disclosed in U.S. Non-Provisional patent application Ser. No. 11/942,764, filed Nov. 20, 2007, and entitled "Vacuum Timing Algorithm for Biopsy Device," the disclosure of which is incorporated by reference herein. Of course, any other suitable components, structures, or configurations may be used. Alternatively, holster (302) may simply lack a user interface altogether.

Holster (302) of the present example is configured to be coupled with a biopsy probe (103), such as biopsy probe (103) described above, to provide a biopsy device (101). In addition, holster (302) is configured to be handheld, such that biopsy device (101) may be manipulated and operated by a single hand of a user (e.g., using ultrasound guidance, etc.). However, it will be appreciated in view of the disclosure herein that holster (302) may be used in a variety of other settings and combinations. By way of example only, holster (302) may alternatively be coupled with biopsy probe (102) instead of biopsy probe (103). As another merely illustrative example, holster (302) may be coupled with a variation of biopsy probe (102) that has a modified needle hub (60) (e.g., a needle hub (60) that is shorter, not configured for firing needle portion (10), etc.).

Either biopsy device (100, 101) may be coupled with a vacuum control module (not shown) that is operable to provide fluids (e.g., vacuum, atmospheric air, saline, pressurized air, etc.), power, and/or commands to biopsy device (100, 101). Suitable examples of such a vacuum control module are disclosed in U.S. Non-Provisional patent application Ser. No. 11/942,764, filed Nov. 20, 2007, and entitled "Vacuum Timing Algorithm for Biopsy Device," the disclosure of which is incorporated by reference herein. Of course, any other suitable components, structures, or configurations may be used.

Alternatively, biopsy device (100, 101) may be provided and used without a vacuum control module. By way of example only, biopsy device (100, 101) may have an on-board vacuum pump (not shown) and/or pressure pump (not shown). Merely exemplary biopsy devices with such on-board pumps are disclosed in U.S. Non-Provisional patent application Ser. No. 11/965,048, filed Dec. 27, 2007, entitled "Vacuum Sensor and Pressure Pump for Tetherless Biopsy Device," the disclosure of which is incorporated by reference herein; and in U.S. Non-Provisional patent application Ser. No. 11/964,811, filed Dec. 27, 2007, entitled "Clutch and Valving System for Tetherless Biopsy Device," the disclosure of which is incorporated by reference herein. Again, though, any other suitable components, structures, or configurations may be used.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A biopsy probe, wherein the biopsy probe comprises:
   (a) a body portion;
   (b) a cannula extending from the body portion, wherein the cannula defines at least one lumen, wherein the cannula comprises a transverse aperture configured to receive tissue, wherein the cannula further comprises a plurality of recessed dimples formed therein;
   (c) a tip located at the distal end of the cannula;
   (d) a first blade extending longitudinally from the tip;
   (e) a second blade extending longitudinally from the tip; and
   (f) a cutter configured to translate relative to the cannula, wherein the cutter is configured to sever tissue.

2. The biopsy probe of claim 1, wherein the tip is formed separately from and joined with the cannula.

3. The biopsy probe of claim 1, wherein the first blade and the second blade are angularly offset by approximately 90 degrees.

4. The biopsy probe of claim 1, wherein the first blade has a first length, wherein the second blade has a second length, wherein the first length is greater than the second length.

5. The biopsy probe of claim 1, wherein the first blade distally terminates at a first distal point at a first axial position relative to the cannula, wherein the second blade distally terminates at a second distal point at a second axial position relative to the cannula, wherein the first distal point is distal to the second distal point.

6. The biopsy probe of claim 1, wherein the first blade has a pair of edges converging at a distal point.

7. The biopsy probe of claim 1, wherein the first blade has a convexly curved distal edge.

8. The biopsy probe of claim 1, wherein the tip and first blade are configured to produce a transverse length of cut in tissue, wherein the cannula has an outer perimeter length about an axis defined by the cannula, wherein length of cut is greater than or approximately equal to the perimeter length of the cannula.

9. The biopsy probe of claim 1, wherein the first blade is integrally formed with the tip.

10. The biopsy probe of claim 1, wherein the first blade is formed separately from and joined with the tip.

11. The biopsy probe of claim 1, wherein the tip further comprises a head, wherein the cannula has a cannula diameter, wherein the head has a head diameter, wherein the head diameter is greater than the cannula diameter.

12. The biopsy probe of claim 1, further comprising a linear motor, wherein the linear motor is operable to controllably fire the cannula distally relative to the body portion.

13. The biopsy probe of claim 1, wherein the tip comprises at least two concave surfaces, wherein the first blade bisects at least one of the at least two concave surfaces.

14. The biopsy probe of claim 13, wherein the at least two concave surfaces comprise four concave surfaces.

15. The biopsy probe of claim 13, wherein the at least two concave surfaces are adjoined at sharp edges, wherein the cannula has an outer perimeter length about an axis defined by the cannula, wherein each of the sharp edges has a length that is greater than or approximately equal to the perimeter length of the cannula.

16. A biopsy probe, wherein the biopsy probe comprises:
(a) a body portion;
(b) a cannula extending from the body portion, wherein the cannula defines at least one lumen, wherein the cannula comprises a transverse aperture configured to receive tissue, wherein the cannula further comprises a plurality of recessed dimples formed therein;
(c) a tissue piercing tip located at the distal end of the cannula, wherein the recessed dimples in the cannula are proximal to the tip; and
(d) a cutter configured to translate relative to the cannula, wherein the cutter is configured to sever tissue.

17. The biopsy probe of claim 16, wherein the cannula has a cannula length, wherein the transverse aperture extends along a portion of the cannula length, wherein at least some of the recessed dimples are located along the same portion of the cannula length as the transverse aperture such that the recessed dimples are positioned to correspond with the position of the transverse aperture.

18. A biopsy probe, wherein the biopsy probe comprises:
(a) a body portion;
(b) a cannula extending from the body portion, wherein the cannula defines at least one lumen, wherein the cannula comprises a transverse aperture configured to receive tissue, wherein the cannula comprises a plurality of recessed dimples formed therein, wherein the recessed dimples are inwardly directed;
(c) a tissue piercing tip located at the distal end of the cannula; and
(d) a cutter configured to translate relative to the cannula, wherein the cutter is configured to sever tissue protruding through the transverse aperture.

19. The biopsy probe of claim 18, wherein the recessed dimples are configured to reduce a contact surface presented by the cannula.

20. The biopsy probe of claim 18, wherein the recessed dimples are configured to reduce drag effects on the cannula as the cannula is inserted in tissue.

\* \* \* \* \*